United States Patent [19]

Lee, Jr.

[11] 4,102,856
[45] Jul. 25, 1978

[54] DENTAL RESTORATIVE COMPOSITIONS AND PROCESS OF USING THEM

[75] Inventor: Henry L. Lee, Jr., Pasadena, Calif.

[73] Assignee: Lee Pharmaceuticals, S. El Monte, Calif.

[21] Appl. No.: 768,765

[22] Filed: Feb. 15, 1977

[51] Int. Cl.² ........................... C08K 3/36; C08K 9/06
[52] U.S. Cl. ................................... 260/42.53; 106/35; 260/998.11
[58] Field of Search ...................... 260/998.11, 42.53; 526/271, 309, 320; 106/35

[56] References Cited

U.S. PATENT DOCUMENTS

| 3,432,478 | 3/1969 | Maz | 526/320 |
| 3,539,526 | 11/1970 | Bomen | 526/320 X |
| 3,663,599 | 5/1972 | Koshimura et al. | 526/320 |
| 3,770,811 | 11/1973 | Lee et al. | 526/309 |

Primary Examiner—Sandra M. Person
Attorney, Agent, or Firm—Irons and Sears

[57] ABSTRACT

Dental restorative compositions are described comprising a finely divided filler mixed with a resin binder that can be activated to cause it to set in situ after application to a tooth surface or within a tooth cavity. The resin binder has as its primary component the reaction product of an alicyclic diacid (or its anhydride) polyfunctional material that has been reacted to form an ester with each of two acrylate or methacrylate materials, which may be the same but that preferably are different.

23 Claims, No Drawings

DENTAL RESTORATIVE COMPOSITIONS AND PROCESS OF USING THEM

FIELD OF THE INVENTION

This invention relates primarily to dental restorative compositions and to methods for using them. More particularly, the invention relates to dental restorative compositions that contain a finely divided filler and a binder that can be activated to cause it to set after it has been applied to a defect in a tooth surface or has been inserted in a prepared cavity in a tooth.

THE STATE OF THE ART

Most composite dental restorative compositions, that are currently in use, are based on diacrylates that contain aromatic groups. Typically, these compositions are made available to the dental profession in the form of kits, with each kit containing two separate containers. The container contents are dispensed in the desired proportions at the same time of use, are mixed, and are then applied to a defect in a tooth surface or inserted in a prepared cavity, and permitted to set.

The compositions ordinarily are prepared in two separate parts, each of which contains a mixture of filler and resin binder, but with a specially formulated catalyst-activator system that becomes effective only when the contents of the two containers are mixed together. Upon admixture, the restorative composition binder sets within a very few minutes, generally to form a solid tooth filling of high compressive strength.

Resin binders based upon the use of one or more diacrylates have often been used in the past because they provide predictable, rapid setting times, good compressive strength, and with the filler, afford an opportunity to match closely the shade of any particular host tooth.

While dental restorative compositions that are based on diacrylates containing aromatic groups generally have proved to be highly satisfactory, particularly with respect to cured compressive strength, tensile strength and flexural strength, there is significant room for improvement in such parameters as polymerization shrinkage, color stability, water sorption, wear resistance and stain resistance.

Early experimental work on direct dental filling compositions, based on the use of acrylate binders, is described in the patents of R. L. Bowen, including U.S. Pat. Nos. 3,066,112, 3,179,623, and 3,539,526. Improved resin binder compositions, based on the use of mixtures of bisphenol A backbone monomers and active aliphatic acrylate monomers, were described by H. L. Lee, Jr., et al., in U.S. Pat. No. 3,539,533. These latter compositions were the first to achieve sustained and noteworthy commercial and professional recognition among dental practitioners. Other U.S. patents, including Lee as a coinventor which also disclose advances in this art, include, for example, U.S. Pat. Nos. 3,730,947, 3,751,399 and 3,769,336.

Diacrylates of the general kind used in connection with the present invention are disclosed for use in paints in U.S. Pat. No. 3,785,849.

SUMMARY OF THE PRESENT INVENTION

In its broadest aspects, the present invention is a dental restorative composition comprising a finely divided filler admixed with a binder that can be activated to set and that comprises a diacrylate of the formula:

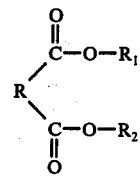

where:

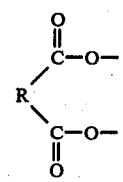

is the residual moiety of an organic alicyclic dicarboxylic acid selected from the group consisting of hexahydrophthalic acid, tetrahydrophthalic acid, and a maleic acid adduct of methylcyclopentadiene, and wherein $R_1$ and $R_2$ are the residual moieties of the same or different hydroxyalkyl or epoxyalkyl esters of acrylic acid or methacrylic acid, respectively.

The adduct of methylcyclopentadiene with maleic acid or its anhydride is available commercially as "Nadic Methyl Anhydride", hereinafter "NMA". The term "Nadic" is a trademark of Allied Chemical Corporation.

While these three kinds of alicyclic o-dicarboxylic acids have been found to be eminently suitable for present purposes, other such acids may also be used such as, for example, some of the substituted hydrogenated phthalic acids such as the lower alkyl-substituted tetrahydro and hexahydrophthalic acids.

These binder materials permit ease of manufacture. When made as hereafter described in more detail, in a stepwise reaction, the production process, which involves exothermic reactions, is more easily controlled. Moreover, the more precise control permits the production of binder compounds with preselected, more uniform viscosities and refractive indices than is feasible otherwise.

When used herein as a generic term (rather than as a part of the name of a specific chemical compound), the term "acrylate" is intended to mean both acrylate and methacrylate.

An acrylate binder, prepared in accordance with the present invention can be cured in the usual way, as by the addition of an activator or accelerator, and a catalyst. Generally, as is customary, dental restorative compositions in accordance with the present invention will be prepared for distribution to the dental profession in a two-container kit, for mixing on demand. The contents of the two containers will include an activator-catalyst system that becomes active upon mixing, to cause the mix to cure within a very short time.

For use, a cavity or fissure is prepared, and then it is filled with a composition of the present invention while that composition remains flowable, so that it can conform to the contours of the cavity or fissure or to that of a matrix or form when such is used. The composition is tamped into place to ensure complete contact, and then is shaped roughly. In some instances, a matrix or form is placed against it. The composition sets rapidly once in place, hardening in situ. It is then finally shaped and polished. Generally, these compositions include finely divided particles of an inorganic filler.

For a direct dental filling composition, a finely divided inorganic filler is mixed with the binder system. The filler generally amounts to from about 40% to about 85% by weight of the composition.

DESCRIPTION OF THE PREFERRED EMBODIMENTS

The particular embodiments of dental restorative compositions that are preferred make use of a primary monomeric material in the binder system that is a diacrylate of an alicyclic dicarboxylic acid selected from the group consisting of hexahydrophthalic acid, tetrahydrophthalic acid, and NMA. To form the desired diacrylate, a two-step process may be advantageously employed, in which the material that furnishes the acid component is reacted first with one material to form an acrylate monoester, and then with a second material, to form the diacrylate.

While the material that serves as the source of the acid is not necessarily the acid or its anhydride, as is well understood by those in this art, the anhydride is a convenient and inexpensive acid source.

In one preferred embodiment of the invention, hexahydrophthalic anhydride is reacted with a hydroxyalkyl acrylate or methacrylate to produce a monoester, which is then reacted with an epoxyalkyl acrylate or methacrylate to produce the diester.

One preferred form of this chemical reaction, using reactants that produce a preferred diacrylate, can be represented in terms of chemical formulae in the following manner:

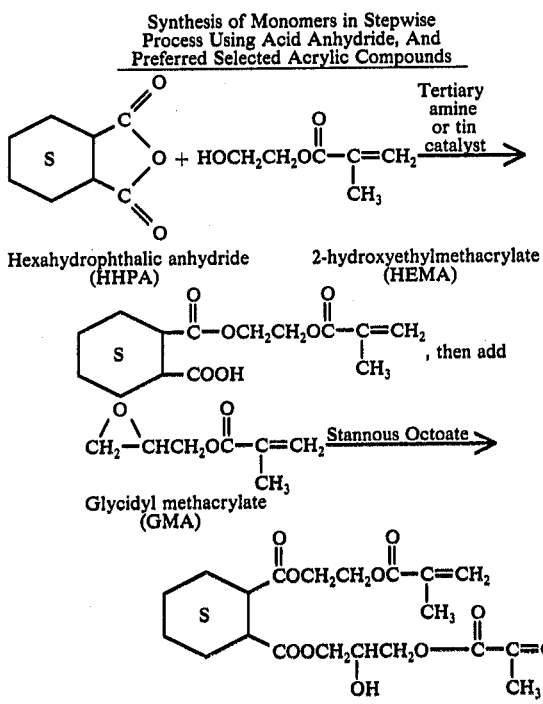

HHPA-HEMA-GMA reaction product (hereinafter "adduct")

In place of the hexahydrophthalic anhydride depicted above, the anhydrides of tetrahydrophthalic acid or of NMA may be used. Similarly, in place of the hydroxyethylmethacrylate, other hydroxyalkyl esters of acrylic and methacrylic acids may be used. Similarly, in place of the glycidyl methacrylate, other epoxyalkyl esters of acrylic and methacrylic acid may be substituted.

While the reaction has been illustrated in terms of the reaction between an acid anhydride and hydroxy-substituted or epoxy-substituted esters, it will be understood that any other conventional technique can be employed for effecting the reaction. Thus, for example, in place of the anhydride, an acyl chloride or dichloride could be used as the reactant to supply the acid material, or similarly, a metal salt or a diisocyanate could be used, together with appropriately modified acrylate reactants, to yield the desired polyacrylate adduct of an alicyclic polycarboxylic acid.

The class of diacrylates described briefly above, and in more detail hereafter, form the primary monomeric material in the binder system for the direct dental filling compositions of this invention. The primary monomeric material may constitute the entire binder system, and should provide at least 20% by weight of the binder system, and preferably from about 60% to about 80% by weight of the binder system. The balance may be a reactive diluent monomeric material such as, for example, ethylene glycol dimethacrylate, diethylene glycol dimethacrylate, triethylene glycol dimethacrylate, other polyglycol dimethacrylates, Bis-GMA, i.e., bisphenol-A-bis-(3-methacryloyl-2-hydroxypropyl) ether, and like monomers that are acceptable for use in the dental composition field.

The polyglycol dimethacrylates are preferred crosslinking monomers because, generally, they have low viscosity and low surface tension, and enhance these properties of the filling composite. This promotes penetration of fissures and bonding to tooth surfaces.

In formulating a dental composition for use as a filling material, a finely divided filler material is mixed with the resin system, in the amount of from about 40% to about 85% by weight of filler based on the entire composition. The filler is generally in the form of fine particles, that may be fibrous, somewhat spherical, or irregular in shape, or a mixture of these.

A composition used as a restorative material in lieu of the common amalgam restoratives of the prior art might, for example, contain approximately 65% and desirably up to about 80% by weight of an inorganic filler. Among the advantages of the resin compositions of the present invention is their ability to carry large amounts of filler material, thus providing restoratives of extremely high compressive strength, low shrinkage and low coefficient of thermal expansion among other desirable properties of a dental restorative material.

The filler may be any finely divided inorganic solid which, when dispersed through the binder system, will give improved structural strength when the binder system is cured. The finely divided filler may have a particle size generally in the range of about 1 micron to 30 microns, and desirably will have the characteristics specified in the U.S. Pat. No. 3,792,531 of Carl J. Rossi. Particularly desirable fillers for use in the composite restoratives of this invention are those which have also been pretreated in accordance with the procedure described in copending application Ser. No. 401,808, of Lee and Orlowski, filed Sept. 28, 1973.

Best results are obtained where the inorganic filler is treated with a keying agent to improve the bond between the organic polymer binder and the surfaces of the finely divided filler particules. Keying agents which have been found to be highly suitable are the ethylenically unsaturated organosilane finishing or keying agents where the filler is fused or amorphous silica, glass, aluminum oxide, or crystalline quartz, and the binder system is of the type described. The finely divided filler may be treated with the keying agent, for example, in the manner described in copending U.S. Pat. application Ser. No. 662,226, of Lee, Stoffey and Orlowski, filed Feb. 27, 1976, which is a continuation of another patent application, Ser. No. 436,680, filed Jan. 25, 1974, which in turn was a continuation of Ser. No. 146,465, filed May 24, 1971.

The binder system is cured by the action of an activator or accelerator, and a catalyst. For most applications, room temperature cure in from about two to about ten minutes is desirable.

The amount of accelerator used depends upon the particular resin compositions which are utilized and the working time which is desired. Generally accelerators can be employed in amounts of 0.001% to 5% by weight of the monomeric materials utilized. In most cases, the amount of accelerator will fall in the range from about 0.5% to 2% by weight of the monomeric materials utilized. Usually about 0.5% to 1% by weight of the binder system of an activator is sufficient. Examples of accelerators which have been used are N,N-dimethyl-para-toluidine, para-toluene sulfinic acid, N-bis(hydroxyethyl)-p-toluidine, para-tolyl diethanolamine and other tertiary amines which are well known in the art.

Catalysts are usually employed in amounts of about 0.2% to about 5% by weight of the monomeric materials. Generally, amounts of about 0.25% to 2.5% by weight of the monomeric materials are satisfactory. Peroxide catalysts are preferably employed in amounts in the range from about 1% to 2% by weight based on the weight of the monomers present. While peroxide catalysts such as benzoyl peroxide are preferred, other catalysts well known in the art may be employed.

It is also recommended that minor amounts of a polymerization inhibitor and/or antioxidant be included in the resin composition. Thus, in order to inhibit unwanted polymerization during extended shelf storage, it is customary to include 60–110 ppm. hydroquinone. An example of an antioxidant employed is 2-tert-butyl-4-methylphenol in an amount of from 0.05% to 1.0% based on the total weight of monomer present in the binder system.

As indicated, the compositions of this invention can be utilized as a restorative filler material, or as dental cements, for example, for bridges and crowns in place of commonly used silicate cements. They may also be used in sealing fissures in tooth surfaces.

One example of a dental restorative composition, in accordance with the present invention, that will set at mouth temperature, to harden within a few minutes, would contain from 0.5% to 1% by weight based on the diacrylate monomer binder system of an accelerator such as N,N-di(2-hydroxyethyl)-para-toluidine; from 1% to 2% by weight of benzoyl peroxide based on the weight of the diacrylate monomer binder system; finely divided silica coated with tris-(2-methoxyethoxy) vinyl silane, in an amount corresponding to about 80% by weight of the final composition. The monomer system may be one such as is described above, or such as is specified in the following specific examples. To modify this for use as a dental fissure sealant, the amount of filler would be reduced to about 65% by weight of the composition.

The filler material containing the catalyst, and the binder system containing the accelerator, are then thoroughly mixed together and promptly placed in a cavity to be filled. The binder will polymerize at mouth temperature to harden within several minutes. Fillings formed in this way from the restorative compositions of this invention have very high compressive strength. An alternative packaging technique involves the use of two parts of a resin-filler mixture, one part containing the catalyst, and the other, the accelerator. Cure is initiated by mixing the two parts in the desired amount.

The invention will now be further illustrated by specific examples. All references to parts and percentages are by weight, unless expressly stated to be otherwise. The temperatures reported are on the Centigrade scale unless otherwise specified.

EXAMPLE 1

The Adduct of Tetrahydrophthalic Acid (THPA) with Hydroxyethyl Methacrylate (HEMA) and Glycidyl Methacrylate (GMA)

A mixture was made in a 12 liter flask of

Table 1 A

| Component | Amount |
| --- | --- |
| HEMA | 1,950 gms. |
| THPA | 2,310 gms. |
| Butylated hydroxy toluene (BHT) (an inhibitor) | 8 gms. |

The mixture was heated to 85° C to 90° C with constant stirring, in an atmosphere of dry air. After 15 hours of reaction in a constantly renewed atmosphere of dry air, the reaction was determined to be about 56% complete. At this point, the following were added:

Table 1 B

| Component | Amount |
| --- | --- |
| GMA | 2,130 gms. |
| Triphenyl phosphine (TPP) | 16.5 gms. |

Over one hour's time, the exothermic reaction raised the temperature of the reaction mixture, with increasing rapidity, until it eventually reached about 120° C, and the flask was then cooled with running water to 60° C. The flask was then heated again to about 85° C to 90° C, and after several hours more of reaction at about 90° C, essentially all of the HEMA was used up. The product composition was about 86% adduct (diester) products, about 1% unreacted THPA, 0.5% water, and 2% other materials. The index of refraction at 22° C was 1.4924, and the epoxy equivalent was 38,334.

The adduct produced can be used as the primary monomer in a binder system for a direct dental filling composition.

The reaction was repeated with more gradual addition of the GMA, in view of the highly exothermic nature of the reaction. The initial reaction mixture was:

Table 1 C

| Component | Amount |
| --- | --- |
| HEMA | 2,006 gms. (2.5% excess) |
| THPA | 2,280 gms. |
| BHT | 8.0 gms. |
| TPP | 16.5 gms. |

After an initial reaction period with heating to 85° C – 90° C, GMA was added in a stepwise fashion. At the first step, 423.5 gms. of GMA were added. The temperature rose to 105° C within 15 minutes, then fell to 90° C–95° C. After 1½ hours, an additional 422.5 gms. GMA were added. The temperature rose about 10° C within 15 minutes, then dropped back to 90° C. After two hours, no free GMA was present, and an additional 498.5 gms. of GMA were added, with a rise in temperature of 4° C – 5° C. After 1 hour, 407 gms. more GMA were added, with no perceptible temperature rise. After 1 hour, the final 379 gms. of GMA was introduced, again with no noticeable change. The total amount of GMA added was thus 2,130 gms.

The reaction mix was heated for a total of 24 hours at 85° – 90° C, after which the residual GMA was 4% - 6%. The product was removed from heat, and the yield was about 100% of the crude adduct product. The epoxy equivalent was 74,633, and the refractive index $n_D^{22}$ was 1.4891, as compared to the theoretical value 1.4850.

This product also can be used in the binder system for dental restorative compositions.

EXAMPLE 2

The Adduct of Hexahydrophthalic Anhydride (HHPA), Hydroxyethyl Methacrylate (HEMA) and Glycidyl Methacrylate (GMA)

The adduct of hexahydrophthalic anhydride, hydroxyethyl methacrylate and glycidyl methacrylate (I), which may be represented as follows:

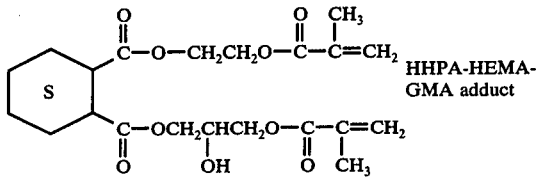

HHPA-HEMA-GMA adduct was synthesized and subjected to preliminary evaluation as a dental restorative.

The adduct was synthesized by a two-step sequence. The non-catalyzed addition of HEMA to HHPA (Equation 1, below) yielded the diester acid (II, below) (or monoester).

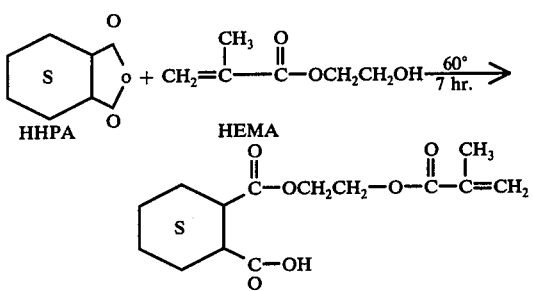

The monoester intermediate reaction point II was then reacted with GMA, the addition being catalyzed by triphenylphosphine (TPP), giving the desired diacrylate adduct product I in very high yield (Equation 2). Both reactions were run without solvents.

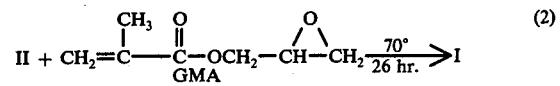

The adduct monomer product I was a viscous oil which was formulated directly, without dilution, into the composite material consisting of a two-paste system (Table 2 A, below).

Table 2 A

| Formulation | | | |
|---|---|---|---|
| Paste A | | Paste B | |
| Amount | Ingredient | Amount | Ingredient |
| 3.0 g | adduct monomer I | 5.5 | adduct monomer I |
| 60 mg | Accelerator | 13.0 g | Other ingredients |
| 10.5 g | Other ingredients | | |

The other ingredients include the finely divided fillers, the inhibitor, catalyst, and other materials conventionally employed in the two-container dental restorative composition, as generally described above.

To use the two-part formulation described in Table 2 A above, the two pastes were mixed in equal proportions, in quantity adequate to fill several simulated test cavities. Mixing brought together the ingredients of the accelerator-catalyst system, to begin the curing process.

The gel time at 24° C was 175 seconds. The ratio of filler to resin was approximately 2.8 to 1. After curing, the compressive strength of 5 samples was averaged and found to be 38,550 psi.

The procedure for carrying out this synthesis was as follows.

A mixture of 15.4 g (0.10 mole) of HHPA and 13.0 g (0.10 mole) of HEMA (dried over molecular sieves) was heated in a 60° C oil bath with magnetic stirring for 7 hours, in a sealed bottle. Upon cooling, the viscous oil product crystallized as a white solid, to give an essentially quantitative crude yield of the intermediate monoester product II, mp. 47° – 52° C, after high vacuum drying for 2 hours to remove residual HEMA. This appeared to be a racemic mixture of the d- and l- forms.

The crude monoester product II (0.10 mole), 14.2 g (0.10 mole) of GMA and 0.11 g (0.25% based on total weight) of TPP were heated at 70° for 26 hours with magnetic stirring in a sealed bottle. The product, a light brown viscous oil, was recovered in essentially quantitative yield.

After each step of the reaction, the structure of the product obtained was confirmed by nuclear magnetic resonance and infrared spectroscopy techniques. The index of refraction of the product at 23° C was observed to be 1.4865.

This adduct material made a good binder, leading to a highly satisfactory dental restorative composition characterized by improved color stability upon exposure to sunlight or other source of ultraviolet radiation.

EXAMPLE 3

Large Scale Synthesis of the Adduct of HHPA, HEMA, and GMA

For a larger scale preparation, larger quantities of HHPA and HEMA were mixed together in equimolar proportions. The mixture was heated at a temperature in the range from about 70° C to about 80° C for 12 hours. At the end of that time, the reaction to form the intermediate monoester product was substantially complete. Some HEMA appeared to be left over, but the amount was not material.

The intermediate monoester product was mixed with an equimolar amount of GMA, and with 0.25 percent of TPP, based on total weight. The mixture was then heated for 24 hours at an elevated temperature in the range from about 75° C to 80° C. At the end of that time, the reaction was essentially completed. The actual yield of the desired adduct product was about 98.5% of theoretical. The product was a brown, viscous oil.

When used as a binder in a dental restorative composition, excellent results were obtained.

EXAMPLE 4

Evaluation of Dental Filling Compositions Based on HHPA-HEMA-GMA Adduct

An adduct of the HHPA-HEMA-GMA configuration was prepared for use as the prime component in a direct dental filling composition. Its viscosity at 25° C, as measured on a Brookfield viscometer, was read as 2,118 cps. (in the range from 2050 cps, to 2200 cps). Its refractive index at 25° C was 1.4860.

Catalyst Paste 4 A

To form the binder for the catalyst paste, the adduct was mixed with an inhibitor, BHT, and with a special formulation of BHT with a material for absorbing ultraviolet radiation. The binder was composed of the materials listed as follows:

Table 4 A

| Ingredient | Parts by Weight |
|---|---|
| HHPA-HEMA-GMA adduct | 100 |
| BHT (inhibitor) | 0.12 |
| UV-9 (U.V. absorber) | 0.56 |

This binder was then mixed with filler and retained for use as catalyst paste 4 A. The filler to binder ratio was 4.0 to 1.0. The filler contained silane-treated silica particles, admixed with benzoyl peroxide (BPO).

Catalyst Paste 4 B

For comparison, a similar catalyst paste was made up, containing a reactive diluent monomer, tetraethylene glycol dimethacrylate (TEGDMA), in the binder. The binder was made up of the following:

Table 4 B

| Ingredient | Parts by Weight |
|---|---|
| HHPA-HEMA-GMA adduct | 90 |
| TEGDMA | 10 |
| Accelerator - (N,N-bis(2-hydroxy-ethyl)-p-toluidine) | 0.12 |
| UV-9 (U.V. absorber) | 0.56 |

The binder was mixed with the same filler material, in the same proportions, and used in the same way as Catalyst Paste 4 A. The resulting paste is identified hereafter as Catalyst Paste 4 B.

These binder systems, whether cross-linkable or not, remained free from polymerization and sedimentation after 3 weeks of storage in an environmental chamber at 37° C and at a relative humidity of 75%.

Neutral Paste 4 C

A neutral paste was prepared for mixing with the catalyst paste. The binder for this paste was made up as follows:

Table 4 C

| Ingredient | Parts by Weight |
|---|---|
| BIS-GMA | 60 |
| TEGDMA | 20 |
| Polyethylene glycol dimethacrylate | 20 |

This resin binder was mixed with accelerator and a silane-treated silica particle filler in a 4.0 to 1.0 ratio of binder to filler. The mixture was held for use as Neutral Paste 4 C.

Neutral Paste 4 D

A second neutral paste was prepared, for use for mixing with a catalyst paste, for evaluation. The binder for this paste was made up as follows:

Table 4 D

| Ingredient | Parts by Weight |
|---|---|
| BIS-GMA | 60 |
| Dimethacrylate of ethoxylated bis phenol A (EBA) | 20 |
| TEGDMA | 20 |

This binder was mixed with accelerator and a silane-treated silica particle filler in a 4.0 to 1.0 ratio of binder to filler. The mixture was held for use as Neutral Paste 4 D.

EVALUATION

For evaluation, dental filling compositions were prepared by mixing together in equal parts:

| Composite | Mixture of Equal Parts of Pastes |
|---|---|
| 4-1 | 4 A, 4 C |
| 4-2 | 4 A, 4 D |
| 4-3 | 4 B, 4 C |
| 4-4 | 4 B, 4 D |

| Composite | Observed Properties Property | Observation |
|---|---|---|
| | Translucency | |
| 4-1 | | 34.5% |
| 4-2 | | 36.5% |
| 4-3 | | 33.0% |
| 4-4 | | 35.0% |
| | $C_{70}$ (a measure of optical properties) (the value for a natural tooth is 0.5 – 0.6) | |
| 4-1 | | 0.67 |
| 4-2 | | 0.67 |
| 4-3 | | 0.65 |
| 4-4 | | 0.65 |
| | Hardness (Rockwell) | |
| 4-1 | | 113.5 |
| 4-2 | | 111.0 |
| 4-3 | | 113.0 |
| 4-4 | | 111.2 |
| | Compressive Strength, 24 hrs. | |
| 4-1 | | 41,058 |
| 4-2 | | 43,704 |
| 4-3 | | 40,847 |
| 4-4 | | 41,446 |

The resistance to discoloration after 24 hours exposure to a sunlamp was also observed. The values for all of the composites were comparable.

EXAMPLE 5

The Adduct of NMA with HEMA and GMA

This adduct was prepared by the stepwise method described in Example 1. Its refractive index at 25° C was 1.4960. The viscosity of the adduct as determined on a Brookfield viscometer at 25° C was read at 6,650 cps. (in the range 6500–6800 cps.). The adduct was used to prepare catalyst pastes, both alone and combined with 10% TEGDMA as in Example 4, except that when used alone, the filler/resin ratio was 3.9/1.0 (79.8% filler based on the composition).

These binder systems remained free from polymerization and sedimentation after 3 weeks of storage in an environmental chamber at 37° C and at a relative humidity of 75%.

When the adduct alone was used as the active binder component, the catalyst paste was identified as 5 A. When the binder was based on diester plus 10% cross-linking diluent (TEGDMA), the catalyst paste was identified as 5 B. These pastes were mixed with equal parts of the neutral paste 4 D, respectively, to permit an observation of their properties.

The mixtures were made up as follows:

| Composite | | Mixture of Equal Parts of Pastes |
|---|---|---|
| 5-2 | | 5 A, 4 D |
| 5-4 | | 5 B, 4 D |
| | Observed Properties | |
| Composite | Property | Observation |
| | Translucency | |
| 5-2 | | 40.0% |
| 5-4 | | 37% |
| | $C_{70}$ | |
| 5-2 | | 0.68 |
| 5-4 | | 0.67 |
| | Hardness (Rockwell) | |
| 5-2 | | 111.0 |
| 5-4 | | 112.0 |

The resistance to discoloration was good.

The resistance to discoloration was good.

EXAMPLE 6

Other Binder Systems; Effect of Diluent Monomers

While the use of the diluent monomer has been illustrated in the examples at the level of 10% by weight of the total amount of the monomeric materials present in the binder system, it may be present over a wide range of values, from a few percent up to about 80% of the weight of the total amount of monomeric components in the binder, depending on the final properties required.

For example, where the primary monomeric material has the configuration, HHPA-HEMA-GMA, the following monomer mixtures have been tested and found to be generally satisfactory, although differing in properties such as viscosity of the binder system and consistency of the filled paste, and in the physical characteristics of the cured composite. In each case, the accelerator, N,N-bis(hydroxyethyl)-para-toluidine, was mixed with the resin system, and the catalyst, with the filler.

Run 6 A

| Component | Parts by Weight |
|---|---|
| HHPA-HEMA-GMA adduct | 60 |
| Ethylene glycol dimethacrylate (EGDMA) | 40 |

The filler used (Filler A) was a finely divided, silane-treated silica, catalyzed with benzoyl peroxide.

This binder system was very viscous. At an 80% level of filler, the consistency of the paste was very thick. Translucency was 42%. $C_{70}$ was 0.76.

Run 6 B

| Component | Parts by Weight |
|---|---|
| HHPA-HEMA-GMA adduct | 60 |
| EGDMA | 30 |
| TEGDMA | 10 |

At an 80% level of Filler A, the paste consistency was satisfactory. Translucency was 37.5%, and compressive strength, 39,330 psi. $C_{70}$ was 0.71 to 0.77.

Run 6 C

| Component | Parts by Weight |
|---|---|
| HHPA-HEMA-GMA adduct | 60 |
| EGDMA | 25 |
| TEGDMA | 15 |

At an 80% level of Filler A, the translucency was 40% and $C_{70}$, 0.74.

Run 6 D

| Component | Parts by Weight |
|---|---|
| HHPA-HEMA-GMA adduct | 100 |
| N,N-bis(hydroxyethyl)-para toluidine | 0.12 |
| UV-9 | 0.56 |

The binder refractive index at 25° C was 1.4860. Gel time was 121 seconds at 23° C, with 80% of Filler A. Translucency was 34.5%, compressive strength 41,058 psi, and hardness, 113.5H. There was no discoloration. $C_{70}$ value was 0.67.

When the primary monomeric diester material was reduced to 90 parts and 10 parts of TEGDMA were substituted, again with 80% Filler A by weight of the total composition, the translucency was 33%, compressive strength 40,847 psi, and hardness, 113H. There was no discoloration. $C_{70}$ value was 0.65.

Run 6 E

| Component | Parts by Weight |
|---|---|
| NMA-HEMA-GMA adduct | 100 |
| N,N-bis(hydroxyethyl)-para-toluidine | 0.12 |
| UV-9 | 0.56 |

The refractive index of the primary monomer at 25° C was 1.4960. Filler A was added at 3.9 parts of filler for each part of the binder system.

Run 6 E was repeated with 10 parts of TEGDMA substituted for 10 parts of the primary monomer, and with a Filler A to binder system ratio of 4.0/1.0. The results in both runs were satisfactory.

EXAMPLE 7

Other Binder Systems

Useful binder systems have been based on adducts of the following configurations:

| |
|---|
| HHPA-HEMA-GMA |
| THPA-HEMA-GMA |
| HHPA-HEMA-HEMA |
| THPA-HEMA-HEMA |

These adducts have been formulated into catalyst pastes for combination with neutral pastes of the kind already described. The properties of the composites thus produced were quite satisfactory.

The HHPA-HEMA-GMA adduct in particular is very stable even when stored in a catalyst paste. All of these binder systems can readily be combined with a wide variety of filler materials, including radioopaque fillers.

GENERAL

One of the advantages of the use of the adducts that constitute preferred embodiments of the present invention is their ease of manufacture. When a two-stage reaction is conducted, as described in the foregoing examples, both steps are exothermic but both steps are easily controlled. The two-step process for producing the adducts facilitates control over product viscosity and also over the refractive index of the product.

Since the acid moiety of the binder molecule is of an alicyclic dicarboxylic acid, good color stability and low water sorption are characteristics of the dental restorative compositions prepared in accordance with this invention. Good filler loading volume is also obtained, together with high compressive strength, high hardness, low shrinkage and other highly desirable physical characteristics.

In preparing adducts for use in binders in accordance with the present invention, the three preferred alicyclic dicarboxylic acid anhydrides, or other substantially equivalent precursors of the acids, are HHPA, THPA, and NMA.

The hydroxyalkyl acrylate or methacrylate, that may be employed in one of the two stages of the preferred two-stage reaction, in the preferred embodiment of the invention, is preferably a hydroxy-substituted lower alkyl acrylate or methacrylate. However, the hydroxy-substitution can be on substantially any convenient and acceptable aliphatic moiety, although alkyl is preferred and lower alkyl is most preferred. Specific examples of suitable materials include hydroxyethyl acrylate, hydroxyethyl methacrylate, hydroxypropyl acrylate, hydroxypropyl methacrylate, hydroxyethoxyethyl acrylate, hydroxypropoxypropoxypropyl acrylate, and the like.

Glycidyl methacrylate has been identified as a preferred epoxyalkyl methacrylate material for use in one of the stages of the preferred reaction technique. Glycidyl acrylate may also be employed, as may other epoxysubstituted aliphatic, or preferably alkyl, or more preferably lower alkyl, acrylates and methacrylates.

When the preferred adduct binder material is prepared in accordance with the two-stage reaction described above, as is preferred, an inert solvent may be employed, but is not necessary. Similarly, a catalyst is not required, but may be used if desired to accelerate the reaction. The second phase of the reaction is preferably the stage in which the epoxy-substituted material is added, and it ordinarily is desirable to add this material in increments, to permit better control over the reaction. In general, proportions are not critical, but when substantially equimolar amounts are employed, stoichiometric yields are usually obtained.

The reaction temperature is not critical, but ordinarily temperatures above 100° C need not be used and, while they may increase the reaction rate, they do tend to increase side reactions.

The adduct monomer binder of the present invention may be formulated in a dental restorative composition without the use of any other binder material. However, good results are obtained even when the binder of the present invention is admixed with another suitable monomer material, such as, for example, certain aliphatic and aliphatic ether diacrylates and polyacrylates, in amounts that may extend up to as high as 80 percent by weight of the total binder monomers present, but that more preferably, represent only a minor proportion of the total binder present. These diluent binder materials may include, for example, diethylene glycol dimethacrylate, triethylene glycol dimethacrylate, tetraethylene glycol dimethacrylate, and the dimethacrylate that is formed by the reaction of methacrylic acid with the diglycidyl ether of butanediol; and, as well, bisphenol-A-bis (3-methacryloyl-2-hydroxypropyl) ether; and other polyacrylate and polymethacrylate binders, particularly those that have proved themselves to be useful in the formulation of dental restorative compositions.

To make use of a binder in accordance with the present invention it is ordinarily mixed with a finely divided filler, a catalyst, and an accelerator. The filler is ordinarily employed in an amount in the preferred range of from about 50% to about 80% by weight of the overall dental restorative composition. Best results are obtained when the filler particles are coated with an agent that promotes bonding, such as, for example, the ethylenically unsaturated organosilane finishing agents, particularly when the filler is formed from fused or amorphous silica, crystalline quartz or the like. Mixtures of particulate filler materials may be used to achieve particular effects. For example, a radio-opaque material may be incorporated in a filler mixture, or opacifying glass may be added. A mixture of particles of silica, quartz, and opacifying glass, for example, can be used to develop a desired selection of physical and cosmetic properties.

Dental restorative compositions made in accordance with the present invention are resistant to staining and discoloration, provide high compressive strengths, low shrinkage on cure, generally low coefficients of expansion, low water absorption, and an acceptable color. The development of color in the acrylate binder can be controlled, during its production, by careful control over the reaction conditions, and particularly by the use of low reaction temperatures, gradual addition of the glycidyl or other epoxy-substituted reactant, and the like. Dental compositions prepared in accordance with the present invention exhibit a uniform and high degree of cure.

The adduct monomers that are prepared in accordance with the present invention, when used in dental restorative compositions, contain sufficient alicyclic structure to impart good hardness, good water resistance, and good color stability to the cured compositions. Moreover, these monomers are especially easy to make, since they can be made rapidly, at low temperatures, with good yields.

While the invention has been described in connection with specific embodiments thereof, it will be understood that it is capable of further modifications, and this application is intended to cover any variations, uses, or adaptions of the invention following, in general, the principles of the invention and including such departures from the present disclosure as come within known or customary practice in the art to which the invention pertains, and as may be applied to the essential features hereinbefore set forth, and as fall within the scope of the appended claims.

What is claimed is:

1. A dental restorative composition comprising a finely divided filler admixed with a binder that can be activated to set and that comprises an adduct of the formula:

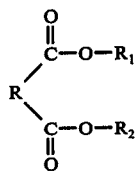

where:

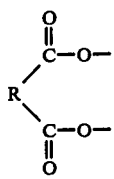

is the residual moiety of an organic alicyclic o-dicarboxylic acid selected from the group consisting of substituted hydrogenated phthalic acids, lower alkyl-substituted hydrogenated phthalic acids, hexahydrophthalic acid, a maleic acid adduct of methylcyclopentadiene, and tetrahydrophthalic acid; and where, $R_1$ consists essentially of the residual moiety of a hydroxyalkyl ester of acrylic or methacrylic acid and $R_2$ consists essentially of the residual moiety of an epoxyalkyl ester of acrylic or methacrylic acid, the linkage of each of $R_1$ and $R_2$ to the adjacent respective oxygen on the residual moiety of the dicarboxylic acid being an ester linkage.

2. A dental restorative composition in accordance with claim 1 wherein $R_1$ and $R_2$ are the residual moieties of hydroxy (lower alkyl) and epoxy (lower alkyl) esters of acrylic or methacrylic acid, respectively.

3. A dental restorative composition comprising a finely divided inorganic filler admixed with a liquid resin binder that can be activated to set and that comprises an adduct of a dicarboxylic acid selected from the group consisting of substituted hydrogenated phthalic acids, lower alkylsubstituted hydrogenated phthalic acids, hexahydrophthalic acid, a maleic acid adduct of methylcyclopentadiene, and tetrahydrophthalic acid, with at least a pair of different materials that provide a acrylate or methacrylate ester substituents, one of which consists essentially of a hydroxyalkyl acrylic or hydroxyalkyl methacrylic residual moiety and another of which consists essentially of an epoxyalkyl acrylic or epoxyalkyl methacrylic residual moiety, the linkage of each of said residual moieties respectively to the dicarboxylic acid being an ester linkage to each of two different carboxyl groups of the acid respectively.

4. A dental restorative composition in accordance with claim 3 wherein the hydroxyalkyl acrylic or hydroxyalkyl methacrylic residual moiety is a hydroxy (lower alkyl) residual moiety.

5. A dental restorative composition in accordance with claim 3 wherein the epoxyalkyl acrylic or epoxyalkyl methacrylic residual moiety is a glycidyl methacrylate residual moiety.

6. A dental restorative composition comprising a finely divided inorganic filler admixed with a resin binder that can be activated to set and that comprises at least 20% by weight of said resin binder of an adduct of the formula:

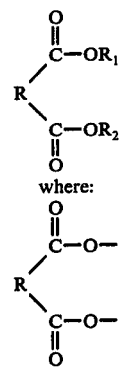

is the residual moiety of an alicyclic o-dicarboxylic acid that is selected from the group consisting of hexahydrophthalic acid, a maleic acid adduct of methylcyclopentadiene, and tetrahydrophthalic acid;

$R_1$ is the residual moiety of an hydroxy (lower alkyl) ester of acrylic or methacrylic acid, and $R_2$ is the residual moiety of an epoxy (lower alkyl) ester of acrylic or methacrylic acid, the linkage of each of $R_1$ and $R_2$ respectively to the adjacent respective oxygen of the dicarboxylic acid being an ester linkage.

7. A dental restorative composition in accordance with claim 6 wherein $R_1$ is the residual moiety of hydroxyethylmethacrylate and $R_2$ is the residual moiety of glycidyl methacrylate.

8. A dental restorative composition comprising a finely divided inorganic filler admixed with a resin binder that can be activated to set and that comprises at least 20% by weight of said resin binder of an adduct of the formula:

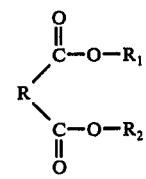

where:

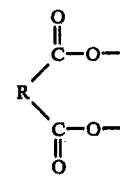

is the residual moiety of hexahydrophthalic acid, $R_1$ is the residual moiety of hydroxyethylmethacrylate, and $R_2$ is the residual moiety of glycidyl methacrylate, the linkage of each of $R_1$ and $R_2$ respectively to the adjacent respective oxygen of the dicarboxylic acid being an ester linkage.

9. A dental restorative composition comprising a finely divided inorganic filler admixed with a resin binder that can be activated to set and that comprises at least 20% by weight of said resin binder of an adduct of the formula:

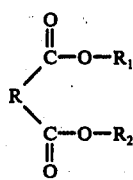

where:

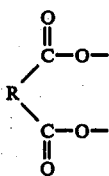

is the residual moiety of a maleic acid adduct of methylcyclopentadiene, $R_1$ is the residual moiety of hydroxyethyl methacrylate, and $R_2$ is the residual moiety of glycidyl methacrylate, the linkage of each of $R_1$ and $R_2$ respectively to the adjacent respective oxygen of the dicarboxylic acid being an ester linkage.

10. A dental restorative composition comprising a finely divided inorganic filler admixed with a resin binder that can be activated to set and that comprises at least 20% by weight of said resin binder of an adduct of the formula:

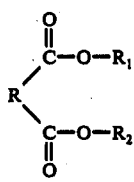

where:

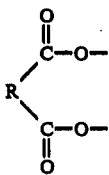

is the residual moiety of tetrahydrophthalic acid, $R_1$ is the residual moiety of hydroxyethyl methacrylate, and $R_2$ is the residual moiety of glycidyl methacrylate, the linkage of each of $R_1$ and $R_2$ respectively to the adjacent respective oxygen of the dicarboxylic acid being an ester linkage.

11. A dental restorative composition comprising a finely divided filler admixed with a resin binder system that can be activated to set, which binder system comprises:

(a), at least 20% by weight of the binder system of an adduct of the formula:

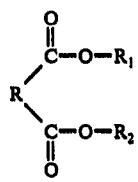

where:

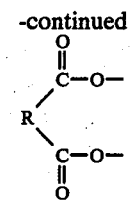

is the residual moiety of an organic alicyclic o-dicarboxylic acid; and $R_1$ consists essentially of the residual moiety of a hydroxyalkyl ester of acrylic or methacrylic acid and $R_2$ consists essentially of the residual moiety of an epoxyalkyl ester of acrylic or methacrylic acid, the linkage of each of $R_1$ and $R_2$ to the adjacent respective oxygen on the residual moiety of the dicarboxylic acid being an ester linkage, (b), at least one diacrylate or dimethacrylate monomer that is copolymerizable with the (a) component above, to cross-link the resin binder upon curing.

12. A dental restorative composition in accordance with claim 11 wherein

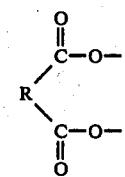

is the residual moiety of an organic alicyclic dicarboxylic acid selected from the group consisting of hexahydrophthalic acid, a maleic acid adduct of methylcyclopentadiene, and tetrahydrophthalic acid.

13. A dental restorative composition comprising a finely divided inorganic filler admixed with a liquid resin binder that can be activated to set, which binder comprises (a), at least 20% by weight of the binder of an adduct of a dicarboxylic acid selected from the group consisting of hexahydrophthalic acid, a maleic acid adduct of methylcyclopentadiene, and tetrahydrophthalic acid, with at least a pair of different materials that provide acrylate or methacrylate ester substituents, one of which is a hydroxyalkyl acrylic or hydroxyalkyl methacrylic residual moiety and another of which is an epoxyalkyl acrylic or epoxyalkyl methacrylic residual moiety, the linkage of each of said residual moieties respectively to the dicarboxylic acid being an ester linkage to each of two different carboxyl groups of the acid respectively, and (b), at least one diacrylate or dimethacrylate monomer that is copolymerizable with the (a) component above, to impart cross-linking to the binder upon curing.

14. A dental restorative composition in accordance with claim 13 wherein the hydroxyalkyl acrylic or hydroxyalkyl methacrylic residual moiety is a hydroxy (lower alkyl) residual moiety.

15. A dental restorative composition in accordance with claim 13 wherein the epoxyalkyl acrylic or epoxyalkyl methacrylic residual moiety is a glycidyl methacrylate residual moiety.

16. A dental restorative composition comprising from about 40% to about 85% by weight of the composition of a finely divided inorganic filler admixed with a liquid monomer binder system that can be activated to set, which binder system comprises (a), from about 60% to about 80% by weight of the binder system of an adduct of the formula:

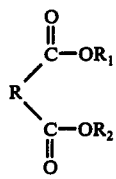

where:

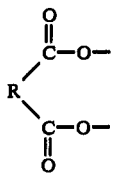

is the residual moiety of an alicyclic o-dicarboxylic acid that is selected from the group consisting of hexahydrophthalic acid, a maleic acid adduct of methylcyclopentadiene, and tetrahydrophthalic acid; $R_1$ is the residual moiety of an hydroxy (lower alkyl) ester of acrylic or methacrylic acid, and $R_2$ is the residual moiety of an epoxy (lower alkyl) ester of acrylic or methacrylic acid; the linkage of each of $R_1$ and $R_2$ respectively to the adjacent respective oxygen of the dicarboxylic acid being an ester linkage, and (b), the balance of the binder system being at least one diacrylate or dimethacrylate monomer that is copolymerizable with the (a) component above, to impart cross-linking to the binder when cured.

17. A dental restorative composition in accordance with claim 16 wherein $R_1$ is the residual moiety of hydroxyethylmethacrylate and $R_2$ is the residual moiety of glycidyl methacrylate.

18. In a method for the direct filling of a cavity in a tooth, that includes filling the cavity with a flowable, settable filling material comprising a finely divided filler and a liquid binder system admixed therewith, and thereafter permitting the material to harden in situ, the improvement comprising utilizing a binder system that comprises (a), at least 20% of the binder system of an adduct

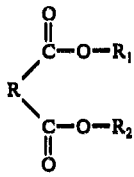

where:

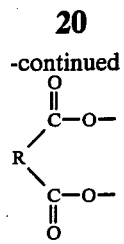

in accordance with claim 1, and (b), at least one diacrylate or dimethacrylate monomer that is copolymerizable with the (a) component above, to cross-link the binder upon curing.

19. In a method for the direct filling of a cavity in a tooth, that includes filling the cavity with a flowable, settable filling material comprising a finely divided filler and a liquid monomeric binder system admixed therewith, and thereafter permitting the material to harden in situ, the improvement comprising utilizing a binder system that comprises (a), at least 20% of the binder system of an adduct of a dicarboxylic acid selected from the group consisting of substituted hydrogenated phthalic acids, lower alkyl-substituted hydrogenated phthalic acids, hexahydrophthalic acid, a maleic acid adduct of methylcyclopentadiene, and tetrahydrophthalic acid, with at least a pair of different materials that provide acrylate or methacrylate ester substituents, one of which consists essentially of a hydroxyalkyl acrylic or hydroxyalkyl methacrylic residual moiety and the other of which consists essentially of an epoxyalkyl acrylic or epoxyalkyl methacrylic residual moiety, the linkage of each of said residual moieties respectively to the dicarboxylic acid being an ester linkage to each of two different carboxyl groups of the acid respectively, and (b), at least one diacrylate or dimethacrylate monomer that is copolymerizable with the (a) component above, to impart cross-linking to the binder upon curing.

20. In a method for the direct filling of a cavity in a tooth, that includes filling the cavity with a flowable, settable filling material comprising a finely divided filler and a liquid binder system admixed therewith, and thereafter permitting the material to harden in situ, the improvement comprising utilizing a filling material composition in accordance with claim 16.

21. In a method for the direct filling of a cavity in a tooth, that includes filling the cavity with a flowable, settable filling material comprising a finely divided filler and a liquid binder system admixed therewith, and thereafter permitting the material to harden in situ, the improvement comprising utilizing a filling material composition in accordance with claim 13.

22. In a method for the direct filling of a cavity in a tooth, that includes filling the cavity with a flowable, settable filling material comprising a finely divided filler and a liquid binder system admixed therewith, and thereafter permitting the material to harden in situ, the improvement comprising utilizing a filling material composition in accordance with claim 3.

23. In a method for the direct filling of a cavity in a tooth, that includes filling the cavity with a flowable, settable filling material comprising a finely divided filler and a liquid binder system admixed therewith, and thereafter permitting the material to harden in situ, the improvement comprising utilizing a filling material composition in accordance with claim 6.

* * * * *